United States Patent [19]

Mentrup et al.

[11] 4,042,713
[45] Aug. 16, 1977

[54] PHARMACEUTICAL COMPOSITIONS CONTAINING A 1-(2-ALKYL-3,4-DIHYDROXY-PHENYL)-2-(PHENYLALKYL-AMINO)-ALKANOL-(1) AND METHOD OF USE

[75] Inventors: Anton Mentrup; Kurt Schromm; Otto Thomä; Karl Zeile, all of Ingelheim am Rhein, Germany

[73] Assignee: Boehringer Ingelheim GmbH, Ingelheim am Rhein, Germany

[21] Appl. No.: 678,612

[22] Filed: Apr. 20, 1976

Related U.S. Application Data

[60] Division of Ser. No. 485,348, July 3, 1974, Pat. No. 3,969,410, which is a continuation-in-part of Ser. No. 217,291, Jan. 12, 1972, abandoned, which is a continuation-in-part of Ser. No. 713,265, Oct. 16, 1967, Pat. No. 3,657,244.

[30] Foreign Application Priority Data

Oct. 18, 1966  Germany .............................. 89417
Oct. 20, 1966  Germany .............................. 89476
Nov. 29, 1966  Germany .............................. 90062

[51] Int. Cl.² ............................................ A61K 31/135
[52] U.S. Cl. .................................................. 424/330
[58] Field of Search .................................... 424/330

[56] References Cited

U.S. PATENT DOCUMENTS 3,139,441  6/1964  Biel .............................. 260/570.6 X
3,341,593  9/1967  Zeile et al. ........................ 260/570.6
3,657,244  4/1972  Mentrup et al. ............... 260/570.6 X

FOREIGN PATENT DOCUMENTS 1,136,549  12/1968  United Kingdom .............. 260/570.6

OTHER PUBLICATIONS

Biel et al., J. Am. Chem. Soc., 76, pp. 3149–3183, (1954).
Heacock et al., Canadian J. Chem., 43, pp. 2535–2539 and 2542, (1965).

*Primary Examiner*—Norman A. Drezin
*Attorney, Agent, or Firm*—Hammond & Littell

[57] ABSTRACT

Pharmaceutical compositions containing as an active ingredient a compound of the formula

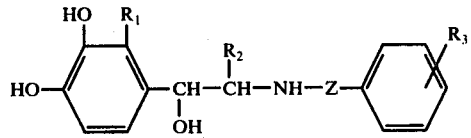

wherein
$R_1$ is alkyl of 1 to 5 carbon atoms,
$R_2$ is hydrogen or lower alkyl,
$R_3$ is hydrogen or hydroxyl, and
Z is alkylene of 2 to 6 carbon atoms, or a non-toxic, pharmacologically acceptable acid addition salt thereof; and a method of using the same as sympathomimetics.

14 Claims, No Drawings

PHARMACEUTICAL COMPOSITIONS CONTAINING A 1-(2-ALKYL-3,4-DIHYDROXY-PHENYL)-2-(PHENYLALKYL-AMINO)-ALKANOL-(1) AND METHOD OF USE

This is a division of copending application Ser. No. 485,348, filed July 3, 1974, now U.S. Pat. No. 3,969,410 granted July 13, 1976; which in turn is a continuation-in-part of application Ser. No. 217,291, filed Jan. 12, 1972, now abandoned; which in turn is a continuation-in-part of application Ser. No. 713,265, filed Oct. 16, 1967, now U.S. Pat. No. 3,657,244.

This invention relates to novel pharmaceutical compositions containing a 1-(2'-alkyl-3',4'-dihydroxy-phenyl)-2-(phenylalkyl-amino)-alkanol-(1) or an acid addition salt thereof, as well as to methods of using the same as sympathomimetics.

More particularly, the present invention relates to novel pharmaceutical compositions containing as an active ingredient a racemic mixture of a compound of the formula

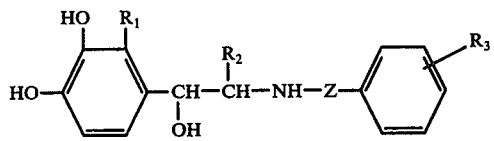

(I)

wherein
  $R_1$ is alkyl of 1 to 5 carbon atoms,
  $R_2$ is hydrogen or lower alkyl,
  $R_3$ is hydrogen or hydroxyl, and
  Z is alkylene of 2 to 6 carbon atoms,
a stereoisomeric component thereof; a diastereoisomeric antipode thereof; or a non-toxic, pharmacologically acceptable acid addition salt of said racemic mixture, stereoisomer or diastereomeric antipode.

The compounds embraced by formula I may be prepared by a number of different methods involving well-known chemical principles, among which the following have proved to be particularly convenient and efficient:

Method A

By reducing a ketone of the formula

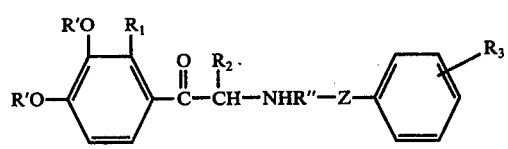

(II)

wherein $R_1$, $R_2$, $R_3$ and Z have the same meanings as in formula I; each R' is hydrogen or a protective group which, if necessary, is subsequently split off, preferably by hydrolysis or hydrogenation, such as acyl or benzyl; or both R', together with each other and the oxygen atoms to which they are attached, form an acetal group whose hydrocarbon moiety preferably contains the diphenylmethylene or cyclohexylidene group; and R" is hydrogen or a protective group, such as benzyl.

The reduction may be carried out with the aid of hydrogen in the presence of a hydrogenation catalyst, such as Raney nickel, platinum or palladium; or also with the aid of complex hydrides, especially sodium borohydride or lithium aluminum hydride; or also by means of the Meerwein-Ponndorf-Verley Reduction.

The various protective groups may be split off all at once or in stepwise fashion, during or after the reduction, by conventional methods.

A starting compound of the formula II may be obtained by customary methods, such as by reacting a compound of the formula

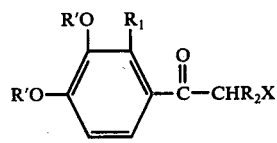

(III)

wherein $R_1$ and $R_2$ have the same meanings as in formula I, R' has the same meanings as in formula II, and X is chlorine, bromine or iodine, with an amine of the formula

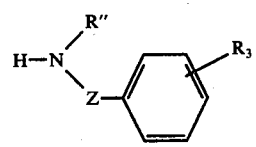

(IV)

wherein $R_3$ and Z have the same meanings as in formula I and R" has the same meanings as in formula II.

Method B

By reducing a compound of the formula

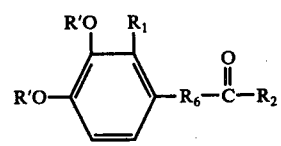

(V)

wherein $R_1$ and $R_2$ have the same meanings as in formula I, R' has the same meanings as in formula II, and $R_6$ is —CO— or —CH(OH)—, in the presence of an amine of the formula

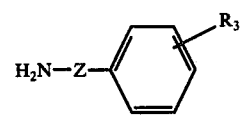

(VI)

wherein $R_3$ and Z have the same meanings as in formula I. The reduction may be effected with hydrogen in the presence of a hydrogenation catalyst, such as Raney nickel or palladium, or with a complex hydride, such as lithium aluminum hydride or sodium borohydride. If the reduction is carried out with the aid of a complex hydride, it is preferred if each R' in the starting compound of the formula V is a protective group, especially benzyl, and these protective groups may be removed in customary fashion subsequent to the reduction reaction. If desired, in those cases where $R_6$ is —CH(OH)—, the Schiff's base formed by the condensation reaction between compound V and amine VI may also be used as the starting compound.

A dicarbonyl compound of the formula V may be obtained by customary methods, such as by oxidation of an analogously substituted aceto-, propio-, butyro- or valero-phenone with selenium oxide.

Method C

By reacting a compound of the formula

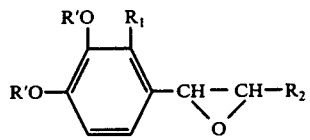
(VIIa)

or
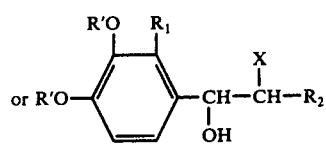
(VIIb)

wherein $R_1$ and $R_2$ have the same meanings as in formula I, R' has the same meanings as in formula II, and X is chlorine, bromine or iodine, or a mixture of compounds VIIa and VIIb, with an amine of the formula IV. If R' and R" in the reaction product thus obtained are protective groups, these may subsequently be removed in conventional fashion.

A compound of the formula VIIa or VIIb may be obtained by known methods, for instance by reducing a haloketone of the formula

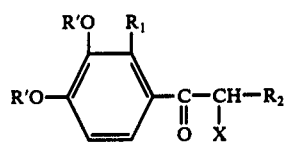
(VIII)

wherein $R_1$, $R_2$, R' and X have the meanings defined above, with sodium borohydride.

Method D

By reacting an amine of the formula

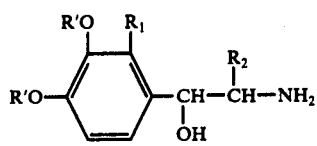
(IX)

wherein $R_1$, $R_2$ and R' have the same meanings as in formula VIIa, under reducing conditions, with a compound of the formula

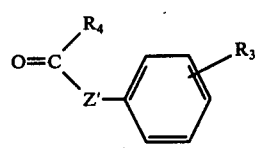
(X)

wherein $R_4$ is hydrogen or straight-chain lower alkyl, Z' is lower alkylene, the sum of the carbon atoms in Z' and $R_4$ being no more than 5, and $R_3$ has the same meaning as in formula I.

The reducing agent may be hydrogen in the presence of a hydrogenation catalyst, such as platinum. If R' in formula IX is a protective group which may be split off by hydrogenation, these protective groups may simultaneously be split off. If R' is acyl, these are removed subsequent to the reduction in customary fashion.

A complex hydride, such as sodium borohydride or lithium aluminum hydride, may also be used as the reducing agent. Under those conditions, it is preferred to use as the starting material a compound of the formula IX wherein R' is a protective group, especially benzyl or diphenylmethyl, and any protective groups present in the reaction product may subsequently be split off in customary fashion.

An amine of the formula IX may be obtained by well-known methods from an analogously substituted isonitrosoketone, cyanohydrin, benzoylcyanide, hydrazine, hydrazide, azidophenone or diazophenone. However, it is not necessary to prepare and isolate the amine IX separately; instead, an analogously substituted starting compound mentioned in the preceding sentence may be subjected, as such, to the reductive substitution reaction, whereby an amine IX is formed in situ and undergoes reaction with compound X.

Method E

For the preparation of a compound of the formula I wherein $R_2$ is hydrogen, by reducing a compound of the formula

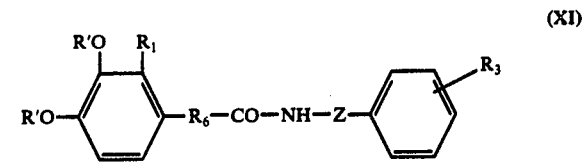
(XI)

wherein $R_1$, $R_3$ and Z have the same meanings as in formula I, R' has the same meanings as in formula II, and $R_6$ has the same meanings as in formula V, preferably with a complex hydride, such as lithium aluminum hydride. Especially suitable as a starting material is a carboxylic acid amide of the formula XI wherein the hydroxyl groups in the 3- and 4-positions on the phenyl ring are protected in the form of acetal or benzylether groupings. These protective groups may be split off again subsequent to the reduction.

Method F

By reacting a compound of the formula

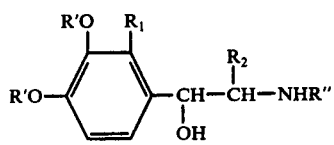
(XII)

wherein $R_1$ and $R_2$ have the same meanings as in formula I and R' and R" have the same meanings as in formula II, with a compound of the formula (XIII)

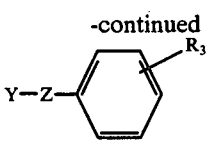

wherein $R_3$ and Z have the same meanings as in formula I, and Y is chlorine, bromine, iodine, arylsulfonyl or alkylsulfonyl. The reaction is advantageously carried out in the presence of an acid-binding condensation agent, such as sodium carbonate or potassium carbonate; however, the amine XII may itself also serve as the acid-binding agent, provided it is present in sufficient excess over and above the stoichiometrically required amount. The protective groups may subsequently be removed in customary fashion.

The compounds of the formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, tartaric acid, fumaric acid, maleic acid, ascorbic acid, benzoic acid, cyclohexylsulfamic acid, 8-chlorotheophylline or the like.

In those instances where methods A through F yield initially an acid addition salt of a compound of the formula I, this salt may be converted into the free base or into another acid addition salt by conventional methods, if desired.

If a starting compound for any of the methods described above exists in stereoisomeric forms, a pure stereoisomer thereof may be used as the starting compound.

If an end product of the formula I contains only one asymmetric carbon atom, a racemic mixture thereof may, if desired, be separated into its optical antipode components by conventional methods. If more than one center of asymmetry are present, the racemates of the diastereomeric pairs of antipodes may be separated from each other, and each pair may in turn be separated into the individual antipodes. For the separation of the mirror image-isomers it is preferred to use fractional crystallization of their addition salts formed with optically active acids, such as dibenzoyl- or ditoluyl-α-tartaric acid.

The following examples illustrate the preparation of compounds of the formula I and non-toxic acid addition salts thereof.

EXAMPLE 1

1-(2'-Methyl-3',4' dihydroxy-phenyl)-2-(γ-phenyl-n-propyl-amino)-ethanol-(1) by method A 97 gm of 2-methyl-3,4-dimethoxy-acetophenone were dissolved in benzene, 25 cc of bromine were gradually added at 75° C., the benzene as distilled off in vacuo, and the residue was diluted with isopropanol, whereby α-bromo-2-methyl-3,4-dimethoxy-acetophenone, m.p. 88° C., crystallized out, which was reacted with 2 mol equivalents of N-benzyl-(γ-phenyl-n-propyl)-amine in acetonitrile at room temperature. The N-benzyl-(γ-phenyl-n-propyl)-amine hydrobromide formed thereby and the solvent were distilled off, the residue was taken up in ether, and the solution was acidified with oxalic acid, yielding α-(N-benzyl-γ-phenyl-n-propylamino)-2-methyl-3,4-dimethoxy-acetophenone hydrogenoxalate, m.p. 118°-121° C. The hydrogenoxalate was dissolved in a mixture of methanol and water (2:1 by volume), and the solution was hydrogenated at 60° C. and 5 atmospheres in the presence of palladized charcoal, yielding a solution of α-(γ-phenyl-n-propyl-amino)-2-methyl-3,4-dimethoxy-acetophenone hydrogenoxalate, which was made alkaline with aqueous ammonia. The free base liberated thereby was dissolved in acetonitrile, and the solution was acidified with ethereal hydrochloric acid, yielding the hydrochloride of α(γ-phenyl-n-propylamino)-2-methyl-3,4-dimethoxy-acetophenone, m.p. 210°-217° C.

50 gm of the hydrochloride thus obtained were admixed with 920 cc of 40% hydrobromid acid, and the mixture was refluxed for 90 minutes and was thereafter allowed to cool, whereby α-(γ-phenyl-n-propylamino)-2-methyl-3,4-dihydroxy-acetophenone hydrobromide, m.p. 179° C., precipitated out. The hydrobromide was converted into the free base, m.p. 130°-138° C., which in turn was converted into ethanol with ethereal hydrochloric acid into its hydrochloride.

30 gm of the hydrochloride of α-(γ-phenyl-n-propylamino)-2-methyl-3,4-dihydroxy-acetophenone thus obtained were dissolved in 300 cc of methanol, and the solution was hydrogenated at atmospheric pressure in the presence of platinum (from 5 gm of $PtO_2$) as a catalyst, the solution being briefly heated to 65° C. at the beginning of the hydrogenation. Thereafter, the catalyst was filtered off, the methanol was distilled off in a stream of hydrogen under a vacuum, and the residue was re-precipitated from dilute hydrochloric acid and then recrystallized from 95% ethanol and dilute hydrochloric acid, yielding 1-(2'-methyl-3',4' dihydroxy-phenyl)-2-(γ-phenyl-n-propyl-amino)-ethanol-(1) hydrochloride, m.p. 176° C., of the formula

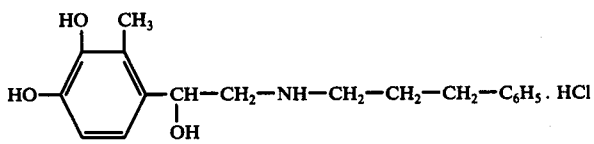

EXAMPLE 2

Preparation of 1-(2'-methyl-3',4'-dihydroxy-phenyl)-2-[2-(p-hydroxy-phenyl)-isopropyl-amino]-ethanol-(1)by method A α-[2-(p-methoxy-phenyl)-isopropylamino]-2-methyl-3,4-dimethoxy-acetophenone hydrochloride, m.p. 205° C., was prepared as reacting α-bromo-2-methyl-3,4-dimethoxy-acetophenone with 2 mol equivalents of N-benzyl-(p-methoxyphenylisopropyl)-amine in ethyl acetate, followed by hydrogenation of the reaction product in methanol at 60° C. at 5 atmospheres in the presence of palladized charcoal as a catalyst, and acidification of the free base hydrogenation product with hydrochloric acid. The hydrochloride thus obtained was boiled for 90 minutes with 48% hydrobromid acid, yielding α-[2-(p-hydroxy-phenyl)-isproylamino]-2-methyl-3,4-dihydroxy-acetophenone hydrobromide, m.p. 115°-125° C., which was converted into the hydrochloride, m.p. 120°–135° C., by dissolving it in water and acidifying the solution with concentrated hydrochloric acid.

20 gm of α-[2-(p-hydroxy-phenyl)-isopropylamino]-2-metyl-3,4-dihydroxy-acetophenone hydrochloride were dissolved in 200 cc of methanol, and the solution was hydrogenated at 20° C., and atmospheric pressure in the presence of platinum (from 2 gm of $PtO_2$) as a catalyst until the theoretical amount of hydrogen had been absorbed. Thereafter, the catalyst was filtered off, 3 gm of benzoic acid were added to the filtrate, and the methanol was distilled off in vacuo. The residue was diluted with 200 cc of ethanol and was then shaken for 45 minutes with 8.4 gm of sodium benzoate, the sodium chloride precipitated thereby was filtered off, the filtrate was evaporated in vacuo, and the residue was stirred with a small amount of ether. The oil obtained thereby crystallized after some time of standing with acetonitrile, the crystals were extracted with hot methyl ethyl ketone, and the extract solution was allowed to cool, whereby a crystalline substance having a melting point of 110° C. separated out, which was identified to be 1-(2'-methyl-3',4' dihydroxy-phenyl)-2-[2-(p-hydroxy-phenyl)-isopropylamino]-ethanol-(1) benzoate of the formula

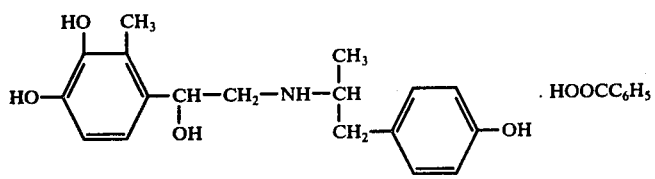

EXAMPLE 3

α-[2-(4'-acetoxyphenyl)-1,1-dimethylethylamino]-2-methyl-3,4-dibenzyloxy-acetophenone hydrochloride, m.p. 205° C., was prepared by reacting α-bromo-2-methyl-3,4-dibenzyloxyacetophenone with 2 mol equivalents of 2-(4'-acetoxyphenyl)-1,1-dimethylethyl-amine. The acetyl group was removed by hydrolysis, and the benzyl groups were split off by hydrogenation, yielding α-[2-(4'-hydroxyphenyl)- 1,1-dimethylethylamino]-2-methyl-3,4-dihydroxyacetophenone, m.p. 235° C. (hydrochloride hydrate), which was reduced as describd in Example 1 to form 1-(2'-methyl-3',4'-dihydroxyphenyl)-2-[2''-(p-hydroxyphenyl)-1'',1''-dimethylethyl-amino]-ethanol-(1) hydrochloride dihydrate, m.p. 195° C., of the formula

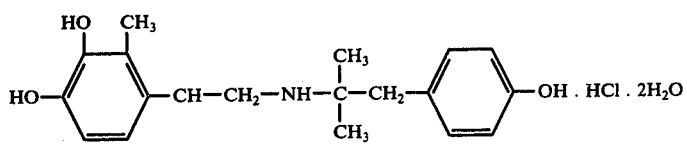

EXAMPLE 4

Starting from α-bromo-2-methyl-3,4-dibenzyloxy-acetophenone and 1,1-dimethyl-3-phenylpropylamine, α-(1,1-dimethyl-3-phenylpropylamino)-2-methyl-3,4-dibenzyloxyacetophenone, m.p. 180° C. (hydrochloride) was prepared. The benzyl groups were split off by hydrogenation and the resulting α-(1,1-dimethyl-3-phenylpropylamino)-2-methyl-3,4-dihydroxyacetophenone hydrochloride, m.p. 209° C., was reduced as described in Example 1 to form 1-(2-methyl-3,4-dihydroxyphenyl)-2-(1,1-dimethyl-3-phenylpropylamino)-ethanol-(1) hydrochloride hydrate, m.p. 100° C., of the formula

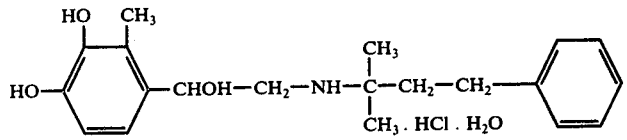

EXAMPLE 5

Using a procedure analogous to that described in Example 4, 1-(2-methyl-3,4-dihydroxyphenyl)-2-(1,1-dimethyl-2-phenylethylamino)-ethanol(1)- hydrochloride, m.p. 179°–181° C., was prepared from α-(1,1-dimethyl-2-phenylethylamino)-2-methyl-3,4-dihydroxyacetophenone hydrochloride, m.p. 228°–231° C., by hydrogenation in the presence of platinum.

The racemic mixtures of the compounds embraced by formula I, their pure stereoisomers, diastereomeric antipode pairs thereof, and non-toxic, pharmacologically acceptable acid addition salts of any of these, have useful pharmacodynamic properties. More particularly, they exhibit sympathomimetic activities in warm-blooded animals, such as mice and rats; especially, they exhibit bronchospasmolytic antipuritic activities and dilate the peripheral blood vessels in warm-blooded animals, such as those above referred to.

Particularly active in this respect are those compounds of the formula I wherein $R_1$ is methyl, $R_2$ is hydrogen, methyl or ethyl, Z is alkylene of 2 to 5 carbon atoms, and $R_4$ is hydrogen or hydroxyl.

For pharmaceutical purposes the compounds of the formula I or their non-toxic acid addition salts are administered to warm-blooded animals topically, perorally or parenterally as active ingredients in customary dosage unit compositions, that is compositions in dosage unit form consisting essentially of an inert pharmaceutical carrier and an effective dosage unit of the active ingredient, such as sprays, tablets, coated pills, granulates, suppositories, ointments, solutions or suspensions. One effective dosage unit of a compound according to

EXAMPLE 6

Tables

The table composition is compounded from the following ingredients:

| | Parts |
|---|---|
| 1-(2'-methyl-3',4'-dihydroxy-phenyl)-1-hydroxy-2-(p-hydroxy-phenethyl-amino)-ethane hydrochloride | 5.0 |
| Lactose, powdered | 35.4 |
| Corn starch, dry | 33.0 |
| Finely divided $SiO_2$ | 5.6 |
| Polyvinylpyrrolidone | 0.6 |
| Magnesium stearate | 0.4 |
| Total | 80.0 |

Compounding procedure

The 1-(2'-methyl-3',4'dihydroxy-phenyl)-1-hydroxy-2-(p-hydroxy-phenethyl-amino)-ethane hydrochloride is thoroughly admixed with the lactose, 25.0 parts of the corn starch and 4.0 parts of the $SiO_2$, and the resulting mixture is uniformly moistened with a 5% ethanolic solution of the polyvinyl pyrrolidone. The moist mass is then passed through a 1 mm. mesh screen. The resulting granulate is dried for about 24 hours at 60° C. in a drying chamber with fresh air circulation. The dry granulate is again passed through a 1 mm-mesh screen. 70.0 parts of this granulate are admixed in a suitable mixer with a mixture consisting of the remainder of the $SiO_2$, the remainder of the corn starch and all of the magnesium stearate, this mixture having previously been passed through a 1 mm screen. The resulting mixture is then compressed into tablets weighing 80 mgm each and containing 5.0 mgm of the active ingredient. These tablets break up in the stomach within 50 seconds.

EXAMPLE 7

2% Inhalation solution

This solution is packaged in 10 ml. bottles, the contents of each bottle being composed of the following ingredients:

| | |
|---|---|
| 1-(2'-methyl-3',4'-dihydroxy-phenyl)-1-hydroxy-2-[α,α-dimethyl-γ-phenylpropyl)amino]-ethane hydrochloride | 200.0 mgm |
| Sodium pyrosulfite | 1.0 mgm |
| Disodium salt of ethylenediamine-tetraacetic acid | 5.0 mgm |
| 1/10 N HCl q.s. ad. pH 3. | |
| Minerals-free water, q.s. ad. | 10.0 ml |

These ingredients form a clear, colorless solution with a pH of 3, which may be dispensed with the aid of an aerosol inhalation vaporizer, having an aerosol output capacity of 12.5 liters per minute for bronchospasmolytic therapy.

EXAMPLE 8

Ampules with hypodermic solution

Each ampule contains the following ingredients:

| | |
|---|---|
| 1-(2'-methyl-3',4'-dihydroxy-phenyl)-2-(γ-phenyl-n-propyl-amino)-ethanol-(1) hydrochloride | 0.5 mgm |
| Sodium pyrosulfite | 0.1 mgm |
| Disodium salt of ethylene-diamine-tetraacetic acid | 0.5 mgm |
| Sodium chloride | 8.0 mgm |
| 1/10 N HCl q.s. ad pH 3. | |
| Distilled water | 1.0 ml |

EXAMPLE 9

Suppositories

The suppositories are compounded from the following ingredients:

| | Parts |
|---|---|
| 1-(2'-methyl-3',4'-dihydroxy-phenyl)-2-[α methyl-β-(p-hydroxyphenyl)-ethyl-amino]-ethanol-(1) benzoate | 5.0 |
| Lactose, powdered | 45.0 |
| Suppository base (cocoa butter) | 1650.0 |
| Total | 1700.0 |

Compounding procedure

The 1-(2'-methyl-3',4'-dihydroxy-phenyl)-2-[α-methyl-β-(p-hydroxyphenyl)-amino]-ethanol-(1)-benzoate is thoroughly blended with the powdered lactose, and the resulting mixture is homogeneously distributed in the molten cocoa butter. The composition is then poured into suppository molds holding 1.7 gm of the composition. Each suppository contains 5 mgm of the active ingredient.

EXAMPLE 10

Starch capsules for peroral administration

The contents of the capsules are compounded from the following ingredients:

| | Parts |
|---|---|
| 1-(2'-methyl-3',4'-dihydroxy-phenyl)-2-[2-(p-hydroxyphenyl)-isopropylamino]-ethanol-(1)-benzoate | 5.0 |
| Lactose | 495.0 |
| Corn starch | 500.0 |
| Total | 1000.0 |

Compounding procedure

The 1-(2'-methyl-3',4'-dihydroxy-phenyl)-2-[2-p-hydroxy-phenyl)-isopropylamino]-ethanol-(1) benzoate is gradually admixed with the lactose. When all of the lactose has been incorporated, the mixture is blended with the corn starch. The resulting mixture is filled with capsules holding 1 gm of the mixture. Each capsule contains 5.0 mgm of the active ingredient.

While the present invention has been illustrated with the aid of certain specific embodiments thereof, it will be readily apparent to others skilled in the art that our invention is not limited to those particular embodiments, and that various changes and modifications may be made without departing from the spirit of the invention or the scope of the appended claims.

We claim:

1. A sympatomimetic pharmaceutical dosage unit composition consisting essentially of an inert pharmaceutical carrier and an effective sympathomimetic amount of a racemic mixture of a compound of the formula $$HO-\underset{HO}{\underset{|}{\bigcirc}}\overset{CH_3}{\underset{|}{-}}CH-CH_2-NH-Z-\underset{}{\bigcirc}-R_3$$
$$\phantom{HO-\bigcirc-}\overset{|}{OH}$$

wherein

R₃ is hydrogen or hydroxyl, and

Z is alkylene of 2 to 5 carbon atoms;

a pure stereoisomer thereof; a diastereoisomeric antipode pair thereof; or a non-toxic, pharmacologically acceptable acid addition salt of said racemic mixture, stereoisomer or diastereoisomeric antipode pair.

2. A composition of claim 1, where said compound is of the formula

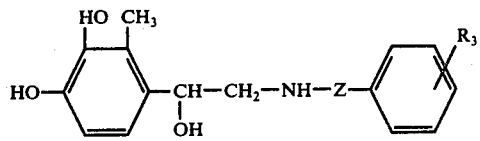

wherein

Z is alkylene of 2 to 5 carbon atoms, and

R₃ is hydrogen or hydroxyl.

3. A composition of claim 2, where said compound is 1-(2'-metyl-3',4'-dihydroxy-phenyl)-2-[(γ-phenyl-n-propyl)-amino]-ethanol-(1) or a non-toxic, pharmacologically acceptable acid addition salt thereof.

4. A composition of claim 2, where said compound is 1-(2'-methyl-3',4'-dihydroxy-phenyl)-2-[2''-p-hydroxy-phenyl)-isopropyl-amino]-ethanol-(1) or a non-toxic, pharmacologically acceptable acid addition salt thereof.

5. A composition of claim 2, where said compound is 1-(2'-methyl-3',4'-dihydroxy-phenyl)-2-[2'''-(p-hydroxy-phenyl)-1'',1''-dimethyl-ethyl-amino]-ethanol-(1) or a non-toxic, pharmacologically acceptable acid addition salt thereof.

6. A composition of claim 2, where said compound is 1-(2'-methyl-3',4'-dihydroxy-phenyl)-2-[(1'',1''-dimethyl-3''-phenyl-n-propyl)-amino]-ethanol-(1) or a non-toxic, pharmacologically acceptable acid addition salt thereof.

7. A composition of claim 2, where said compound is 1-(2'-methyl-3',4'-dihydroxy-phenyl)-2-[(1'',1''-dimethyl-2''-phenyl-ethyl)-amino]-ethanol-(1) or a non-toxic, pharmacologically acceptable acid addition salt thereof.

8. The method of stimulating the sympathetic nervous system of a warm-blooded animal in need of such stimulation, which comprises administering to said animal an effective sympathomimetic amount of a racemic mixture of a compound of the formula

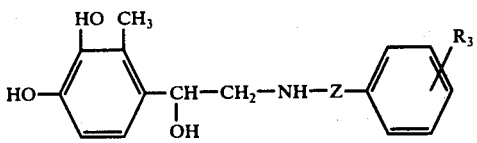

wherein

R₃ is hydrogen or hydroxyl, and

Z is alkylene of 2 to 5 carbon atoms, a pure stereoisomer thereof; a diastereoisomeric antipode pair thereof; or a non-toxic, pharmacologically acceptable acid addition salt of said racemic mixture, stereoisomer or diastereoisomeric antipode pair.

9. The method of claim 8, where said compound is of the formula

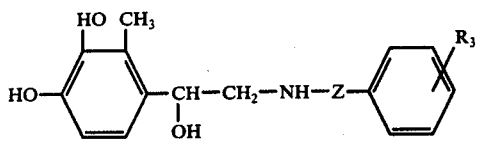

wherein

Z is alkylene of 2 to 5 carbon atoms, and

R₃ is hydrogen or hydroxyl.

10. The method of claim 9, where said compound is 1-(2'-methyl-3',4'-dihydroxy-phenyl)-2-[(γ-phenyl-n-propyl)amino]-ethanol-(1) or a non-toxic, pharmacologically acceptable acid addition salt thereof.

11. The method of claim 9, where said compound is 1-(2'-methyl-3',4'-dihydroxy-phenyl)-2-[2''-(p-hydroxy-phenyl)-isopropyl-amino]-ethanol-(1) or a non-toxic, pharmacologically acceptable acid addition salt thereof.

12. The method of claim 9, where said compound is 1-(2'-methyl-3',4'-dihydroxy-phenyl)-2-[2'''-(p-hydroxy-phenyl)-1'',1''-dimethyl-ethyl-amino]-ethanol-(1) or a non-toxic, pharmacologically acceptable acid addition salt thereof.

13. The method of claim 9, where said compound is 1-(2'-methyl-3',4'-dihydroxy-phenyl)-2-[(1'',1''-dimethyl-3''-phenyl-n-propyl)-amino]-ethanol-(1) or a non-toxic, pharmacologically acceptable acid addition salt thereof.

14. The method of claim 9, where said compound is 1-(2'-methyl-3',4'-dihydroxy-phenyl)-2-[(1'',1''-dimethyl-2''-phenyl-ethyl)-amino]-ethanol-(1) or a non-toxic pharmacologically acceptable acid addition salt thereof.

* * * * *